(12) United States Patent
Mize et al.

(10) Patent No.: US 6,803,235 B1
(45) Date of Patent: Oct. 12, 2004

(54) METHODS OF GENERATING INFORMATION ABOUT MATERIALS PRESENT IN COMPOSITIONS AND ABOUT PARTICULATES PRESENT IN FLUIDS UTILIZING A MICROSCOPE

(75) Inventors: John D. Mize, Spokane, WA (US); Russell B. Gore, Spokane, WA (US); Ronald H. Fleming, Spokane, WA (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/595,583

(22) Filed: Jun. 15, 2000

(51) Int. Cl.[7] ............................................. G01N 31/00
(52) U.S. Cl. .......................... 436/2; 436/75; 436/145; 436/46; 436/164
(58) Field of Search ............................. 436/2, 75, 145, 436/46, 164; 204/298.12, 192.2; 250/307, 310

(56) References Cited

U.S. PATENT DOCUMENTS

| | | | |
|---|---|---|---|
| 3,674,926 A | * 7/1972 | Dewey et al. | 348/138 |
| 4,232,970 A | * 11/1980 | Sawamura et al. | 356/39 |
| 4,584,078 A | * 4/1986 | Nakanouchi et al. | 204/192.2 |
| 4,697,080 A | * 9/1987 | King | 250/307 |
| 4,980,203 A | * 12/1990 | Dabosi et al. | 427/252 |
| 5,409,517 A | * 4/1995 | Satou et al. | 75/228 |
| 5,477,049 A | * 12/1995 | Kitamura | 250/307 |
| 5,494,743 A | * 2/1996 | Woodard et al. | 204/192.14 |
| 5,502,306 A | * 3/1996 | Meisburger et al. | 250/310 |
| 5,665,223 A | * 9/1997 | Bogdan | 208/138 |
| 6,001,227 A | 12/1999 | Pavate et al. | 204/298.12 |

FOREIGN PATENT DOCUMENTS

WO  WO 99/27150  6/1999

OTHER PUBLICATIONS

Udler et al. "Tungsten–Titanium Sputtering Target Technology", Advanced Materials Division, Technical Note 203, 1994.*
http: ??www.iamaterials.com/sputter/stargets.htm, International Advanced Materials, 1999.*
http://www.pechineyhighpurity.com/html/faq.htm, Jan. 14, 2002.*
http://www.encyclopedia4u.com/a/aqua–regia.html, ©2004 Encyclopedia4U.com.*

* cited by examiner

*Primary Examiner*—Yelena G. Gakh
(74) *Attorney, Agent, or Firm*—Wells St. John P.S.

(57) ABSTRACT

The invention encompasses a method of generating information about materials in a composition. A reagent is utilized to dissolve portions of the composition, and thereafter is filtered through a substrate which is then scanned with a microscope using automated displacement of the substrate to obtain data about the non-dissolved portions at locations along a grid pattern. Information about the size and quantity of the non-dissolved portions of the composition is generated. The invention also encompasses a method of generating information about impurities present in a metal composition. Metallic portions of the composition are selectively dissolved relative to impurities to form a solution. The solution is filtered through a substrate which is then scanned with a microscope to obtain data about a darkness of the impurities relative to a background. The data is processed to generate information about the size, quantity and type of the impurities.

5 Claims, 7 Drawing Sheets

FIG. 5

METHODS OF GENERATING INFORMATION ABOUT MATERIALS PRESENT IN COMPOSITIONS AND ABOUT PARTICULATES PRESENT IN FLUIDS UTILIZING A MICROSCOPE

TECHNICAL FIELD

The invention pertains to methods of generating information about materials present in compositions, and in particular aspects pertains to methods of generating information about inclusions, impurities and/or other components present in metal compositions. The invention also pertains to methods of generating information about particulates present in fluids.

BACKGROUND OF THE INVENTION

There are numerous applications in which it is desirable to obtain information about materials present in a composition. For instance, there are applications in which relatively high purity metal is desired, and in which it is accordingly also desired to obtain information about any impurities present in the metal composition. An exemplary application in which relatively high purity metals can be desired is the formation of sputtering targets. Targets can be formed of, for example, aluminum; aluminum+0.5% copper; copper; copper+from 1 to 100 ppm silver; and aluminum+0.5% copper+0.2% silicon. The targets are preferably "high purity", and accordingly are preferably at least 99.995% pure relative to the desired constituents therein. A second application in which high purity materials are desired is in the formation of solders, which can comprise, for example, one or more of lead, tin and silver.

A difficulty in forming targets, or any other high purity material, is that some level of impurity is generally within the material. The type and quantity of the impurity can determine if the impurity can be tolerated within the material, or if the impurity destroys the material for an intended purpose. For instance, it is common for impurities to be introduced during fabrication of sputtering targets from high purity metals. Such impurities can be introduced, for example, during the casting of the metals into a billet. Specifically, casting can use carbon or ceramic containers, such as crucibles and troughs. A small amount of material sometimes transfers from the containers into the metal. Impurities can also be introduced at processing steps other than casting. For instance, target materials can contact silicate or other oxides (such as, for example, aluminum oxide) during fabrication of sputtering targets, and accordingly various oxides can be introduced into the target material.

Impurity particles (such as, for example, carbon particles and/or oxide particles) can be problematic in sputtering target applications. For instance, a particle of impurity can result in an arc into target material proximate the particle. Such arc can cause displacement of relatively large particles of the material. The large particles can then deposit on a substrate wafer to cause so-called splattering on the substrate wafer. The splattering can be problematic in that it forms a less conformal and uniform coating on a substrate than does material which has not been splattered. As microelectronic devices become increasingly smaller, there is increasingly less tolerance for splattering.

The amount of splattering caused by impurities in a target material can be a function of the type of impurity, size of impurity, and quantity of the impurity. For instance, conductive impurities (like carbon) can, in some instances, be less problematic that insulative impurities (like oxides) in that the conductive impurities may be less likely to generate arcs. Further, large impurities can be more problematic than small impurities, in that large impurities can tend to cause more or larger splatters than small impurities. Finally, numerous impurities tend to be more problematic than less numerous impurities, in that numerous impurities will tend to cause more splattering events than would less numerous impurities.

Because the problems caused by inclusions and other impurities can vary depending on the type, size and quantity of impurities within a material, it is desirable to quantitate the impurities within a material by type, size and prevalence. Such quantification can be particularly useful during fabrication of sputtering targets if the quantification occurs after a metal is cast into a billet, and before the metal has been fabricated into a target. Specifically, if a problematic number, size and/or type of impurities are found in a cast material, the material can be identified as being inadequate for target fabrication before the time and expense of target fabrication have been invested into the material. Further, if type, quantity and/or size of impurities are identified within a cast material, such can provide clues as to the source of the impurities. Accordingly, such can enable improvement in a process of casting target materials to avoid introduction of impurities in future processes. Additionally, identification of quantity, size and/or type of impurities in materials can serve as a quality control test.

Another exemplary time when it can be particularly useful to quantitate target material impurities by size, prevalence and/or type is after the material has been formed and utilized as a target. Specifically, if the material is found to perform less than adequately as a target, it would be desirable to subject the material to analysis to determine if the problems associated with the target are caused by particular impurities within the target material.

For the above-described reasons, it would be desirable to develop methods for quantitating impurities in metal materials which could identify one or more of size, type and prevalence of the impurities. The above-described application of determining impurities relative to metal materials is but one of many applications wherein it is desired to identify specific components in particular materials. Accordingly, it would be further desirable to develop methods which were applicable to identifying components of not only metal materials, but also to materials other than metals.

SUMMARY OF THE INVENTION

In one aspect, the invention encompasses a method of generating information about materials (such as inclusions and other impurities, or such as desired components) present in a composition. A reagent is utilized to dissolve at least some of the composition (for purposes of interpreting this disclosure and the claims that follow, the term "reagent" is to be understood to encompass one or both of a reactant and a solvent, unless it is specifically indicated otherwise). The dissolved composition is filtered through a substrate, and portions of the composition are retained on the substrate during the filtering. After the filtering, the substrate is scanned with a microscope. The scanning comprises automated displacement of the substrate relative to an observing portion of the microscope along a pattern (the pattern can be a grid, and can be any shape, including circular or rectangular). The microscope obtains data about the retained portions at locations along the pattern. Automated image processing generates information about one or more of the size, type and quantity of the retained portions of the composition.

In another aspect, the invention encompasses a method of generating information about impurities present in a metal composition. A reagent is utilized to selectively dissolve metallic portions of the composition relative to at least some impurities present in the metal composition. The dissolved metallic portions form a solution with the reagent. The impurities comprise at least two different types, with one of the at least two types being a first type and the another of the at least two types being a second type. The solution is filtered through a substrate. At least some of the first and second types of the impurities are retained on the substrate during the filtering. After the filtering, the substrate is scanned with a light microscope. The scanning comprises automated displacement of the substrate relative to an observing portion of the microscope along a grid pattern. The microscope obtains data about the impurities at locations along the grid pattern. The data includes a relative darkness (i.e., a contrast) of the impurities as compared to a background defined by the substrate. The first type of impurities are darker than the background, and the second type of impurities are lighter than the background. The data is processed to generate information about the size, quantity and type of the impurities.

BRIEF DESCRIPTION OF THE DRAWINGS

Preferred embodiments of the invention are described below with reference to the following accompanying drawings.

FIG. 8 is a diagrammatic top view of a filter similar to that of FIG. 7, and illustrating a grid pattern utilized in accordance with a method of the present invention.

FIG. 9 is a diagrammatic, cross-sectional view of a microscope apparatus incorporated into a system of the present invention.

DETAILED DESCRIPTION OF THE PREFERRED EMBODIMENTS

The invention encompasses methods which can be utilized for generating information about materials present in various compositions. In particular aspects, the invention encompasses methods for generating information about inclusions and other impurities present in metallic compositions. A process encompassed by the present invention, and which can be utilized for generating information about impurities present in metallic compositions, is described with reference to a flow chart in FIG. 1. At initial step 10 of the FIG. 1 process a sample is cut and weighed. The sample can comprise, for example, a portion of a cast metal billet, or a portion of a sputtering target. In an exemplary process, the sample is cut to form a block having a weight of from about 13 grams to about 14 grams. The cutting can utilize a rigid blade saw to alleviate smearing along a surface of the block, and also to alleviate particle entrainment within a surface of the block. An exemplary sample block 100 is shown in FIG. 2, and is shown to comprise an outer surface 102. It is noted that although block 100 is shown to have a rectangular shape, the invention encompasses forming block 100 to have other shapes. For instance, block 100 can be cylindrical, circular, or a wire (such as, for example, a soldering wire). Block 100 will preferably not be a cored sample of a material. It is found that cored samples tend to collect particulates along their smeared sides which can be difficult to remove.

If block 100 comprises a metal, it can comprise, for example, one or more of aluminum, copper, lead, tin and antimony. In particular applications (such as, for example, when block 100 is from a sputtering target composition or solder), block 100 can comprise a high purity metal, and thus can consist essentially of one or more of aluminum, copper, lead, tin and antimony. Block 100 can further comprise impurities, such as, for example, carbon-containing impurities or oxide-containing impurities (such as, for example, silicon dioxide or aluminum oxide) dispersed throughout the metal as inclusions within metal block 100. Additionally, block 100 can comprise non-metallic materials purposefully provided within the metal materials of the block. For instance, if block 100 is from a sputtering target composition, such non-metallic materials can comprise silicon.

Figure 1:
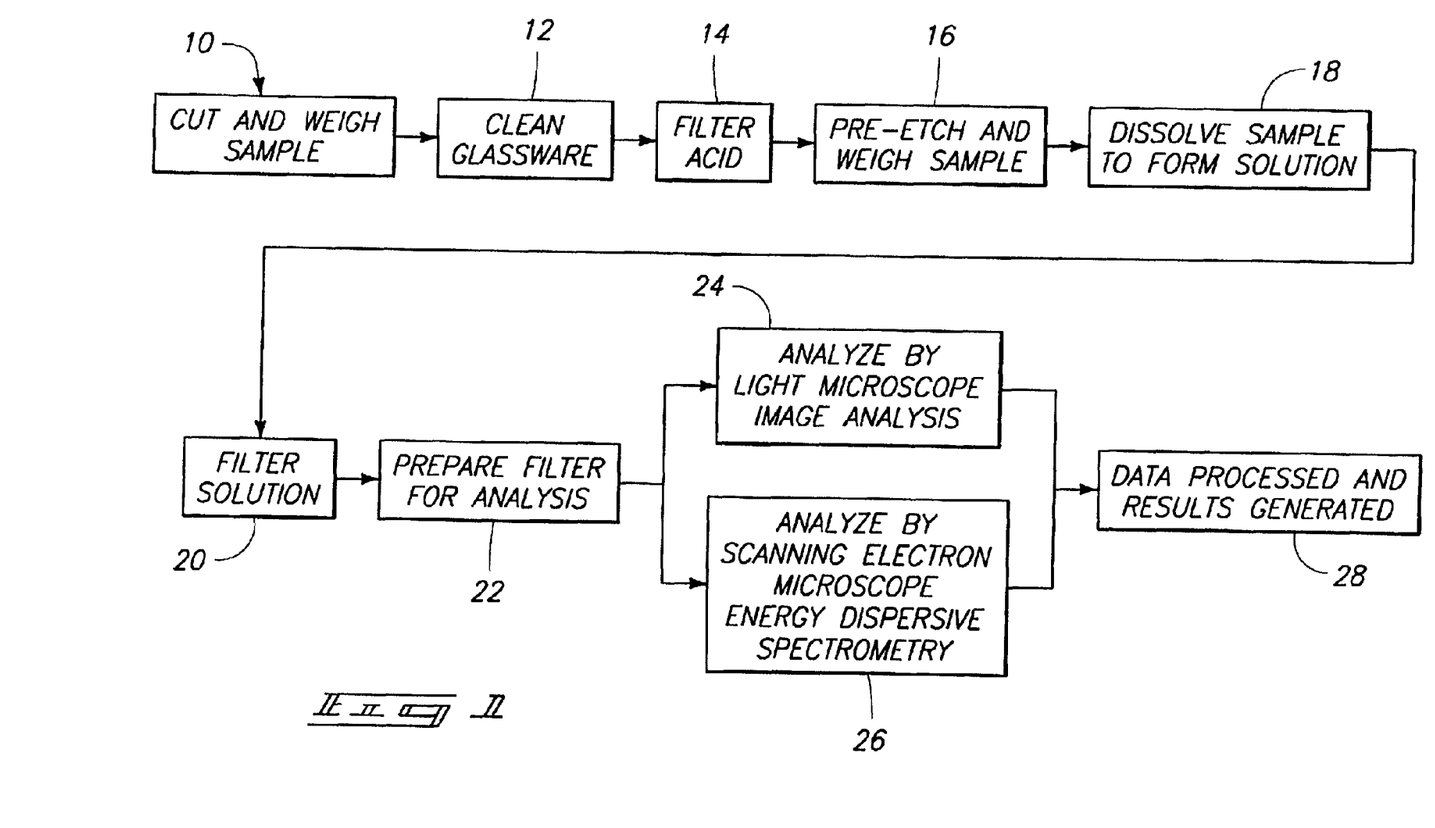
FIG. 1 is a flow chart diagram of a method of the present invention.
Figure 2:
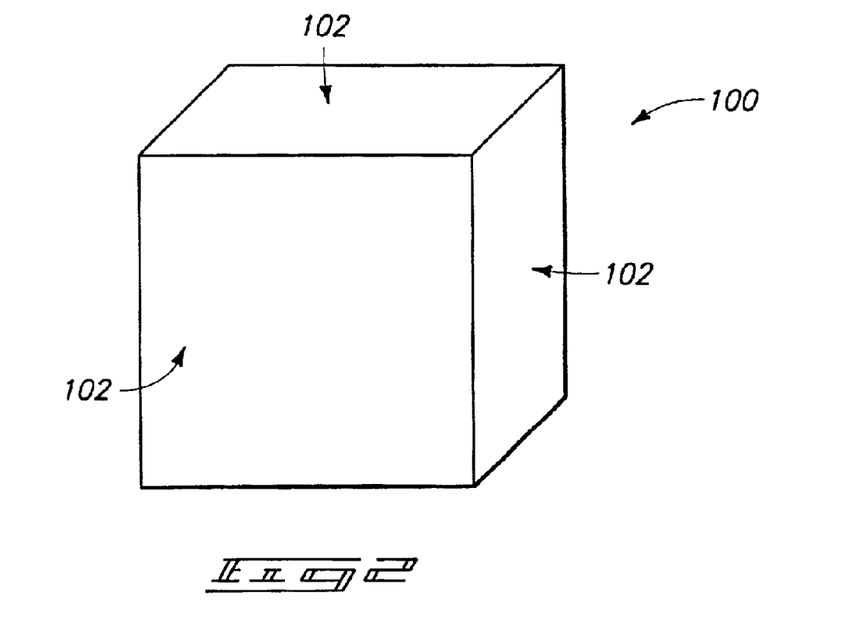
FIG. 2 is a diagrammatic view of a block of material at a preliminary processing step of a method of the present invention.

Referring again to the flow chart of FIG. 1, glassware is cleaned to alleviate contamination being transferred from the glassware to analyzed materials at subsequent process steps of the present invention. The glassware can encompass vessels, such as, for example, beakers, and Erlenmeyer flasks. The glassware can be cleaned by, for example, ultrasonic cleaning utilizing Buehler Ultranet Sonic Cleaning Solution™ available from Buehler of Lakebluff, Ill. The cleaning can comprise, for example, scrubbing of the glassware while soaking with the Ultranet Sonic Cleaning Solution™, followed by sonication of the glassware for 5–6 minutes, and subsequent rinsing of the glassware with 0.2 micron filtered deionized water. The glassware is preferably cleaned the same day as it is used. Referring to step 14 of FIG. 1, an acid is prepared and filtered. If the metal which is to be analyzed comprises one or more of aluminum, lead, antimony and silver, the acid can comprise one or more of hydrochloric acid, acetic acid, and nitric acid. In particular applications of the present invention, the acid can comprise 3 parts hydrochloric acid (with the hydrochloric acid initially being from about 36% to about 38%, by weight, with water); about 1 part nitric acid (with the nitric acid initially being about 70% by weight with water); and about 1 part deionized water. Alternatively, for samples comprising aluminum alloys an acid can comprise 5 parts HCl (with the HCl initially being 36% to 38% HCl in water): one part nitric acid (with the nitric acid initially being about 70% by weight with water): and about 5 parts water. In applications in which the analyzed sample is predominately copper (such as, for example, if the sample consists essentially of copper); the acid can comprise 1 part nitric acid (with the nitric acid initially being 70% nitric acid in water) and 1 part water.

The HCl, acetic acid and HNO₃ are typically twice filtered through a 0.4 micron filter before mixing with other components of the above-described acids, and the deionized water is typically filtered through a 0.2 micron filter before mixing (the water is typically filtered through a 0.2 micron in-line filter, and all water utilized in procedures of the present invention is preferably filtered through a 0.2 micron in-line filter).

Figure 3:
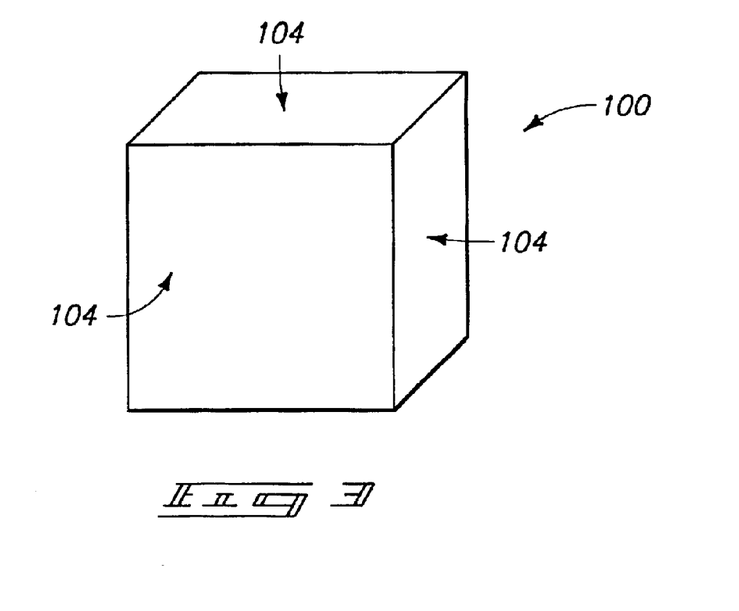
FIG. 3 is a view of a portion of the FIG. 2 block of material at a processing step subsequent to that of FIG. 2.

At step 16 of the FIG. 1 process, the samples are pre-etched, and weighed after the pre-etch. The pre-etching comprises submerging the block 100 of FIG. 2 in a first acid to remove a first outer surface of the block and expose a new (or second) outer surface. The pre-etch can remove contaminates associated with an outer surface of the block that formed on the surface during or after cutting of the block from a material, and which accordingly do not accurately reflect a composition within the block. The pre-etch is preferably done within a portion of the acid from step 14, and can comprise, for example, submerging block 100 within the acid for a time of from about 5 minutes to about 10 minutes at room temperature. The pre-etch preferably removes at least about a fifth of the mass of block 100, so that the mass of material remaining after the pre-etch can be, for example, from about 9 to about 11 grams. Block 100 is shown in FIG. 3 after the pre-etch, and accordingly is shown to be smaller than it was in FIG. 2. Also, the block 100 in FIG. 3 has a new outer surface 104 which was exposed upon removal of the first outer surface 102 (FIG. 2) by the pre-etch.

After the pre-etch, block 100 is preferably removed from the acid, and rinsed in deionized water that had been filtered through a 0.2 micron filter. Block 100 is then dried and weighed.

Referring to step 18 of the FIG. 1 process, the block 100 of FIG. 3 is dissolved in a second acid to form a mixture (indicated in FIG. 1 as a solution). Although step 18 refers to "dissolving" of the block, it is to be understood that the invention encompasses embodiments in which at least some portions of the block are dispersed within the acid, but in which a single phase solution is not formed from the dispersed portions. For instance, if silicon is present in the block, the silicon will typically form a suspension with the above-described acid solutions of the present invention. If it is desired to dissolve the silicon, such can be accomplished by using HF dissolve the silicon (the silicon can, for example, be dissolved after a filtration step that is described below). For purposes of interpreting this disclosure and the claims that follow, the term "dissolve" is to be understood to encompass formation of colloids, molecular solutions and mechanical suspensions, as well as formation of single phase solutions.

The second acid can have the same composition as the acid mixtures utilized for the pre-etch. In an exemplary embodiment of the invention, the sample block 100 consists essentially of non-alloyed aluminum, and the second acid is formed by mixing 200 mls of HCL (36% to 38% by weight with water) with 40 mls of nitric acid (about 70% by weight with water) and 200 mls of water. The block 100 of non-alloyed aluminum is placed within the acid and maintained at a temperature above 80° C. until the aluminum is dissolved (typically 10 to 24 hours). Once dissolution is complete, a clear or slightly yellow solution is formed, with no residual metal or bubbling observed.

In another exemplary embodiment of the invention, block 100 consists essentially of an aluminum/copper alloy, and is dissolved in the same HCl:HNO₃:H₂O acid as described above. Dissolution of the aluminum/copper alloy will typically occur within about 1 hour. The dissolution can be initiated at room temperature, but will frequently reach a temperature of above about 80° C. due the exothermic reaction of the copper and acid. Again, once dissolution is complete there will be no residual metal or bubbling observed within the solution. The solution is typically a light yellow upon dissolving the aluminum/copper alloy.

In yet another exemplary embodiment of the invention, block 100 consists essentially of copper, and is placed in an acid which comprises 220 mls of nitric acid and 220 mls of deionized water. The copper generally dissolves within from about 1 to about 1½ hours. The dissolution can be initiated at room temperature, but will frequently reach a temperature of above about 80° C. due the exothermic reaction of the copper and acid. After dissolution of the copper is complete, the acid solution is blue to blue-green, with no residual bubbling.

The acid dissolution occurring at step 18 dissolves some components of a composition, but does not dissolve at least some other components present within the composition. The term "dissolving" is utilized in referring to step 18 to indicate that components of block 100 are dispersed, solubilized, or otherwise fluidized, and not necessarily that such components form a one-phase solution with the reagent.

Figure 4:
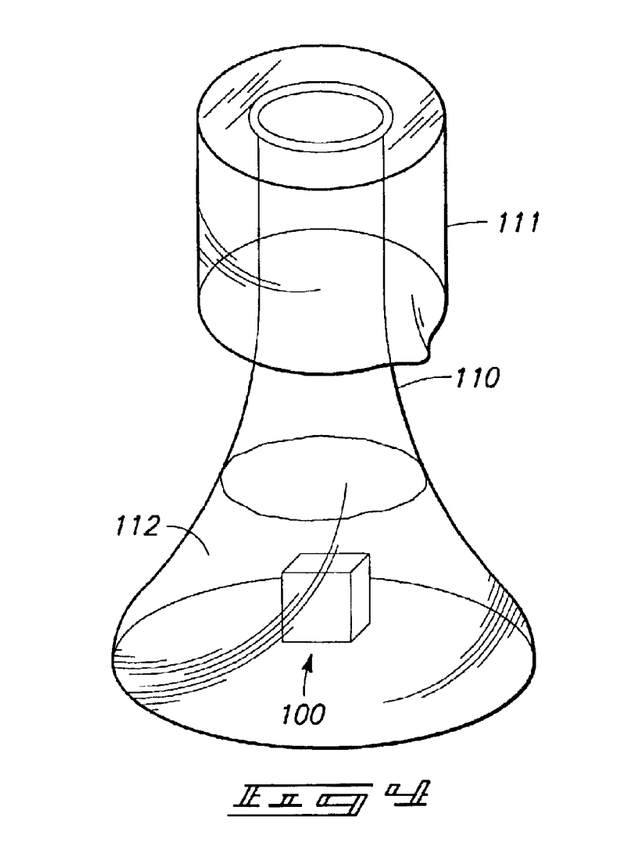
FIG. 4 is a diagrammatic, oblique view of a vessel utilized in a processing step subsequent to the step of FIG. 3.
Figure 5:
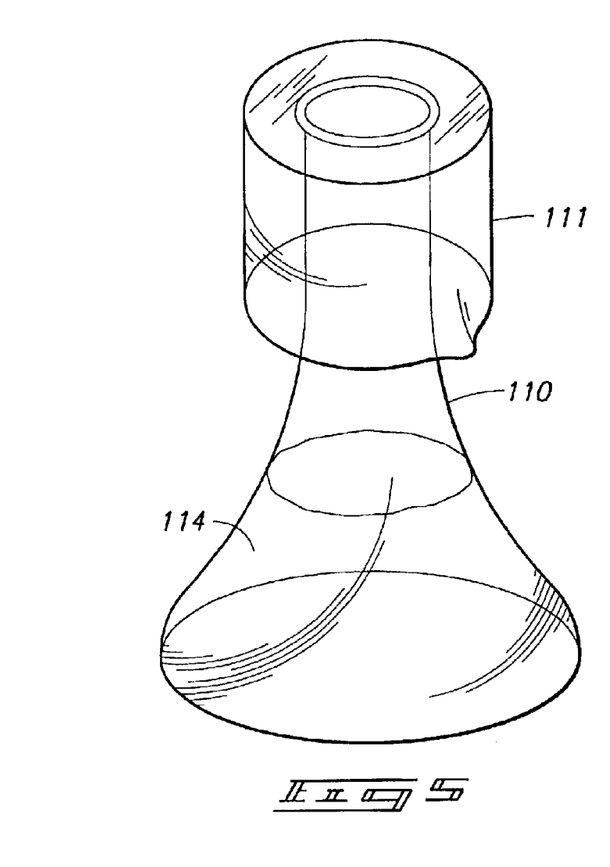
FIG. 5 is a view of the FIG. 4 vessel shown at a processing step subsequent to that of FIG. 4.

The processing associated with step 18 of FIG. 1 is shown diagrammatically in FIGS. 4 and 5. Specifically, FIG. 4 shows a vessel 110 comprising an acid 112, and further shows block 100 submerged within the acid. A lid 111 (shown as an inverted beaker) is provided over vessel 10 to alleviate contamination of acid 112 by environmental particles. FIG. 5 shows the vessel 110 after dissolution of material 100 is complete. Accordingly, block 100 (FIG. 4) is no longer visible, and has dissolved within acid 112 (FIG. 4) to form a solution 114. Accordingly, acid 112 functions as a solvent for portions of the composition of block 100.

Referring to step 20 of the FIG. 1 process, the solution 114 of FIG. 5 is filtered through a substrate. In an exemplary process, solution 114 is filtered through a 0.4 micron filter (i.e., a filter having pores which are predominately 0.4 microns or less in maximum dimension) utilizing a 25 millimeter vacuum filtering assembly. Once solution 114 has been completely filtered, about 150 mls of deionized water (which had been previously filtered through a 0.2 micron filter) is utilized to rinse vessel 110, as well as to rinse sides of the filter assembly. At least some of the non-dissolved materials present within solution 114 are retained on the filter. Specifically, if the filter comprises a maximum pore size of 0.4 microns, then non-dissolved materials larger than 0.4 microns will be retained on the filter, while particles having dimensions less than 0.4 microns will be allowed to pass through the filter.

Although liquid 114 is described as a solution, the invention also comprises embodiments in which the liquid is a suspension or other dispersion. In such embodiments, a pore size of the filter can be chosen to allow some non-dissolved portions of the dispersion through the filter, while retaining other non-dissolved portions on the filter. For instance, if liquid 114 comprises a suspension of silicon in HCl and/or HNO₃, and further comprises particulates larger than the suspended silicon, the pore size can be chosen to allow suspended silicon to pass through the filter while retaining the larger particulates on the filter.

Figure 6:
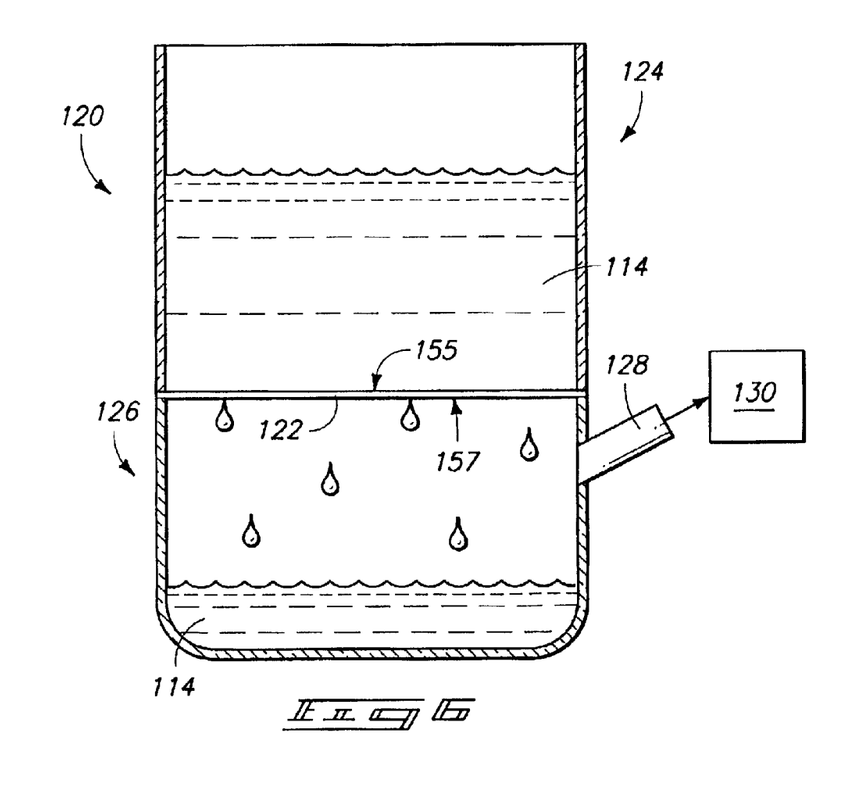
FIG. 6 is a diagrammatic, cross-sectional view of a filtration apparatus utilized in a processing step subsequent to that of FIG. 5.

An exemplary vacuum filtering device 120 is shown schematically/diagrammatically in FIG. 6. Device 120 comprises a filter 122 separating an upper portion 124 of the device from a lower portion 126. Filter 122 comprises an upper surface 155 and a lower surface 157. A port 128 is provided and attached to a vacuum source 130 to reduce a pressure in lower chamber 126 relative to a pressure in upper chamber 124. Solution 114 is provided in upper chamber 124 and pulled through filter 122 into lower chamber 126, with non-dissolved impurities being retained on upper surface 155 of filter 122 as solution 114 passes therethrough. It is noted that filtered deionized water can be utilized to rinse material from glassware surfaces and onto the filter so that particulates which may have been retained on glassware surfaces can be transferred to the filter.

Referring to step 22 of FIG. 1, the filter from step 20 is prepared for further analysis of impurities retained thereon. Specifically, apparatus 120 (FIG. 6) is disassembled and filter 122 removed therefrom. Filter 122 is shown diagrammatically in FIG. 7. Filter 122 comprises a darkened central region 150 where solution 114 has passed therethrough, and a lighter peripheral region 152 surrounding central region 150 (the darkened central region is provided for illustrative purposes only; it is to be understood that in particular embodiments of the invention the central region can appear the same as the peripheral region, and in other embodiments the central region can appear different (either lighter or darker) than the peripheral region). Peripheral region 152 can be, for example, a portion of filter 120 pinched between upper portion 124 and lower portion 126 of assembly 120 (FIG. 6). It is noted that the invention encompasses other embodiments (not shown) wherein an entirety of a filter surface is exposed to a filtered solution 114. It is also noted that although the portion 150 of filter 122 which was exposed to solution 114 is shown as a circular portion, the invention encompasses other embodiments (not shown) wherein portion 150 has a non-circular shape.

Figure 7:
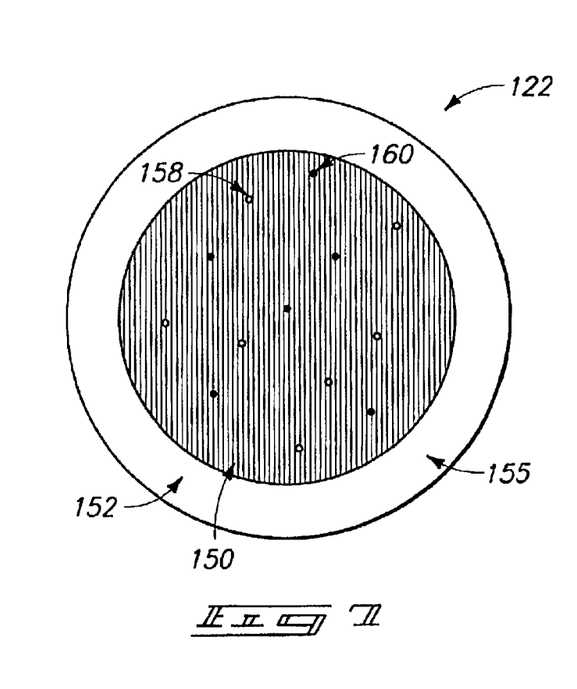
FIG. 7 is a diagrammatic top view of a filter shown at a processing step subsequent to that of FIG. 6.

At least some of the non-dissolved materials present in solution 114 are retained on upper surface 155 of filter 122, and such particles are shown as particles 158 and 160.

Filter 122 is next prepared for microscopic examination. For instance, if the filter is to be analyzed utilizing a light (or optical) microscope, the filter is placed on a frosted-glass microscope slide with surface 155 facing upwardly. Subsequently, a clear microscope slide is placed over surface 155, and the filter/slide combination is placed in an oven set at about 60° C. for about 1 hour to dry the filter and slides. The filter and slides are then removed from the oven, and immersion oil is provided between the back of the filter and the frosted-slide (typically one drop is provided), and further provided between the top of the filter and the clear slide (again, typically one drop is provided). The slide/filter/immersion oil package is then allowed to stand for from about 2 minutes to about 3 minutes, and subsequently the slides are taped together utilizing, for example, adhesive tape.

If, on the other hand, the filter is to be analyzed with a scanning electron microscope, the filter is placed so that bottom surface 157 of the filter is on a conductive carbon tape. Top surface 155 is then exposed to a sputter-coater, and coated for about 12 seconds. An exemplary sputter-coater is the Denton Desk II Sputter Coater™ (available from Denton Vacuum, Inc™, of Morristown, N.J.).

Referring to steps 24 and 26 of the FIG. 1 process, filter 122 is analyzed by either light microscope image analysis or scanning electron microscopy. In particular embodiments of the invention, particles identified by light microscopy can be picked from the filter and subsequently analyzed by electron microscopy. Also, the invention encompasses embodiments wherein two filters are prepared to analyze a composition; with one of the filters being subjected to light microscopy and the other to electron microscopy.

The microscopic analysis of filter 122 preferably utilizes automated scanning across at least a portion of surface 155 of filter 122. The term "automated" is utilized herein to refer to a process wherein one or more actuators are utilized to displace filter 122 relative to an observing portion of a microscope (with the term "observing portion" referring to, for example, the lens of a light microscope), rather than utilizing manual methods of displacing the substrate. The term "automated" can also refer to automatic focussing of the microscope, and/or to automatic image processing. The automatic image processing can include automated identification and/or characterization of particles. However, it is to be understood that the invention also encompasses embodiments wherein manual methods are utilized, instead of automated methods, for one or more of the above-discussed steps.

In particular automated applications, filter 122 can be displaced relative to a lens of a light microscope by moving the lens relative to the filter, the filter relative to the lens, or both the lens and the filter relative to one another.

FIG. 8 illustrates an exemplary grid pattern which can be utilized in scanning across a surface of filter 122. The grid pattern is labeled to show an order at which various locations along the grid are scanned. Note that an exemplary scanning process comprises displacement(s) of substrate 122 relative to an observing portion of a microscope along a horizontal axis (labeled X in FIG. 8), subsequent displacement by 1 unit along an axis "Y" perpendicular to the axis "X", and then horizontal displacement(s) back along the axis X, with such displacements along "X" and "Y" being repeated until an entirety of the grid pattern has been analyzed. In a particular embodiment, filter 122 is scanned by a light microscope, and adjacent points of the grid are separated from one another by 1.5 mm. The microscope has a field of view of about 400 microns by about 530 microns (with an exemplary field of view illustrated as 170 in FIG. 8). Accordingly, at least about 10% of the surface of flow pattern area 150 is sampled, which is determined to be a statistically representative sampling of the surface. In other embodiments, at least 5% of the surface can be sampled, and in yet other embodiments the amount of surface area 150 which is sampled is in a range of from greater than 0% to 100%. It is preferred to obtain a statistically representative sampling of the total area of flow pattern 150 as such can enable a quantitative relation of information gained from the sampling back to the composition of block 100 (FIG. 2).

The grid pattern of FIG. 8 comprises a substantially octagonal outer periphery which is superimposed on a substantially circular outer periphery of the flow pattern. The shown grid pattern is an exemplary shape, and other shapes (not shown) are encompassed by the present invention. If the flow pattern had an outer periphery that was other than substantially circular in shape, it could be desirable to utilize a grid pattern having a different shape than that shown in FIG. 8. It is also noted that although uniform steps are shown between all points of the exemplary grid of FIG. 8, the invention encompasses other embodiments (not shown) wherein at least some of the steps are of a different size than others of the steps.

Referring to step 28 of FIG. 1, data obtained from the microscopic analysis is processed and results are generated from the data. The results generated from the data can include information about the size, type and/or quantity of impurities retained on filter 155, and can be extrapolated to determine information about the size, type and/or quantity of impurities within the sample 100 (FIG. 2) that was initially analyzed.

FIG. 9 is a diagrammatic view of a system 200 encompassed by the present invention which can be utilized for automated scanning of a filter. System 200 comprises a microscope 202 (although the shown microscope is configured as a light reflecting microscope, it is to be understood that that the invention encompasses other embodiments (not shown) in which, for example, a light transmitting microscope is utilized), with microscope 202 comprising a lens 204, a stage 206, and a light source 208. System 200 further comprises a motor to 210 coupled with stage 206 and configured to move stage 206 in a direction "Y", and another direction "X" perpendicular to "Y" (with direction "X" being shown in FIG. 8, and not shown in FIG. 9). In operation, filter 122 (shown diagrammatically, and typically provided between microscope slides (not shown)) is placed on a window (not shown) in stage 206, and light from source 208 is reflected off of a surface of filter 122 and to lens 204. The lens can be autofocussed relative to the filter surface at each step of a grid pattern. The placement of filter 122 on stage 206 can be referred to as "mounting" of the filter to the stage, and can comprise clamping or otherwise securing the filter to the stage.

The light reflected from the surface of filter 122 passes out of lens 204 and to a detector 212 which is configured to detect and quantitate an image passing from microscope to 202. Detector 212 can comprise, for example, a charge coupled device (CCD) array. The light passing from microscope 202 comprises data about impurities located on filter 122, and detector 212 digitizes such data. An exemplary process of the present invention utilizes 200× magnification with a light microscope and image processing with about 0.8 microns per pixel. The digitized data is transferred to an automatic image processor 216 which analyzes the data and generates information about the size, type, shape and/or quantity of impurities from the data. The information obtained by processor 216 is subsequently transferred to an output device 218 which can comprise, for example, a display terminal or a printer.

Processor 216 can be a computer and image processor, and controls a second processor 214. Second processor 214 is a motor controller, and is shown controlling motor 210. Motor 210 is utilized to move stage 206 so that points of the grid pattern of FIG. 8 are aligned with lens 204. Processor 214 controls motor 210 as the motor is utilized to automatically displace the filter along the grid pattern. Processor 216 is configured to correlate a grid position with the data obtained from detector 212. The data obtained from detector 212 is subjected to digital image processing by processor 216. For purposes of interpreting this disclosure and the claims that follow, "digital image processing" refers to a process comprising the following three steps:

(1) an image is recorded as a 2-dimensional array of pixels, with each pixel being associated with a magnitude of a measured property;

(2) the pixels are sorted by their associated magnitudes of the measured property to identify pixels of interest (with pixels of interest being defined as those having a magnitude of the measured property within a specified range or above a specified threshold); and (3) patterns are identified within the distribution of the pixels of interest (for instance, if two or more pixels of interest correspond to locations that are physically adjacent to one another in a scanned image, the pixels could be patterned together as identifying a common particle).

The digital image processing can further comprise autofocus of a microscope prior to data acquisition, and contrast enhancement of features in recorded images (with contrast enhancement including, for example, utilization of algorithms that enhance distinction of feature edges relative to background).

Although the shown embodiment comprises a motor 210 coupled with only the stage, alternative embodiments (not shown) can couple the motor to lens 204 so that the displacement of the filter relative to the microscope comprises movement of the lens either in combination with, or alternatively to, movement of the stage.

Referring again to FIG. 7, it is noted that surface 155 can appear gray under the microscope within the region 150 where solution 114 (FIG. 6) has passed through filter 122. The gray filter provides a background against which particles 158 and 160 are observed. It is further noted that particles 158 and 160 comprise 2 different types of particles, with particles 158 being lighter than the background, and particles 160 being darker than the background. In practice, it is found that particles comprising a high carbon content tend to be darker than a background filter, whereas particles comprising a high oxide content (such as, for example, oxides of aluminum or silicon) tend to be light relative to the background. In a preferred aspect of the present invention, the data passed from detector 212 to processor 216 is analyzed to distinguish particles which are darker than a background from particles which are lighter than the background. Accordingly, processor 216 can subject the data to a binary sort routine to separately generate information about size and quantity of particles which are darker than the background, and information about size and quantity of particles which are lighter than the background. In typical operation, an image is analyzed for particles darker than the background, and such particles are catalogued by size and position by processor 216. Next, the image is re-analyzed for particles lighter than the background, and such particles are catalogued by size and position by processor 216.

The information acquired by the above-described procedure can be useful in categorizing the possible composition of the particles. The information can be displayed as a histogram showing particles by one or more of type, size and aspect ratio (with an aspect ratio of 1 indicating a circular cross-section, and other aspect ratios indicating elliptical cross-sectional shapes). Additionally, once particle quantity and size is determined, the volume of particles in the original sample can be calculated by assuming that the thickness of a particle (in the Z-direction normal to X and Y) is equal to its width. The volume of particles found on a filter should be approximately proportional to the volume of particles present in a sampled material. Once the volume of particles present in a sampled material is estimated, it can be expressed as particle volume per unit volume of the originally sampled material. If it is assumed that dark particles are primarily carbon, the concentration of carbon in the sampled material can be estimated. Further, if it is assumed that light particles are primarily oxides, the amount of oxygen present as oxide inclusions in the sampled material can be estimated. The assumptions that dark particles are primarily carbon and light particles are primarily oxides have been experimentally verified for particular applications of the present invention.

Although the invention is described for characterization of particles which appear light relative to the background and particles which appear dark relative to the background, the invention further encompasses modifications to determine differences in intensity of particles relative to one another, rather than relative to a background. For instance, two different types of particles may exist which are both darker relative to the background, but which are of different intensities relative to one another. Also, it is noted that the invention can utilize contrast mechanisms other than gray-scale, and can utilize, for example, color, fluorescence, response to electrons, photons, x-rays, particle beams, etc. Further, although the invention is described relative to two particle types, it is to be understood that the invention can be utilized for distinguishing amongst more than two types of particles if, for example, the particles are compared to one another, the gray-scale is sub-divided into more than two categories, or multiple colors are utilized and compared. Also, it is to be understood that the invention can be used in applications without the above-described particle differentiation, such as, for example, applications in which the invention is utilized to find any particles different than background, and is not utilized to sort amongst the particles.

In addition to encompassing methods wherein a background is colored or shaded to enable sorting of particles, the invention also encompasses methods wherein one or more particles are chemically or physically modified (for example, stained or otherwise modified relative to their light absorbing characteristics) to enhance their contrast and accordingly enhance sorting of the particles. Such physical modification can occur, for example, after the particles are retained on a filter. In addition to, or alternatively to, modification of the particles, a light source could be altered to modify absorption characteristics of a particle. For instance, filtered or polarized light could be utilized. Additionally, light could be utilized which invoked emission, such as, for example, fluorescence, from particular chemical constituents of particles.

The apparatus of FIG. 9 can utilize a Clemex 640C™ microscope analyzer having an autostage controller box, coupled with Clemex Vision™ software (with the Clemex 640C™ and Vision™ software being available from Clemex Technologies, Inc.™ of Quebec, Canada), and further coupled with a Nikon Epiphot™ Metallograph (available from Buehler of Lakebluff, Ill.). In such application, components 202, 210, 212, 214 and 216 are encompassed by the Clemex 640C™, Nikon Epiphot™ and Vision™ packages.

The processor 216 can further include a software package utilized for manipulation of processed image data. An exemplary software package is Excel™, available from Microsoft™ Corporation, U.S.A.

The system of FIG. 9 is an exemplary system encompassed by the present invention. Other systems encompassed by the present invention can be formed by substituting or combining components shown in FIG. 9. For instance, the light microscope 202 shown in FIG. 9 can be substituted with an electron microscope, such as, for example, a scanning electron microscope. If a scanning electron microscope were utilized instead of the light microscope, particles would typically not be categorized as light and dark relative to a background, but instead could be analyzed by secondary or backscattered electrons, or with x-rays which identified elemental compositions.

The filter 122 described with reference to FIGS. 6 and 7 is described as having a pore size of 0.4 microns. Such pore size is particularly useful when the filter is subsequently subjected to light microscopy, as it can be more difficult to accurately detect and quantify length parameters for particles less than about 2 micrometers, and it can be useful to reject particles having lengths which are not at least 2 micrometers when analyzing for such particles by light microscopy. If other forms of microscopy are utilized, such as, for example, electron microscopy, and if smaller particles can be accurately detected and quantified for size by the other forms of microscopy, then it can be desirable to utilize pore sizes less than 0.4 microns. Also, it is noted that the invention can utilize filters and other substrates comprising or defining pore sizes larger than 0.4 micrometers, such as, for example, when separating large inclusions (or other particles) from suspensions of smaller particles.

Figure 10:
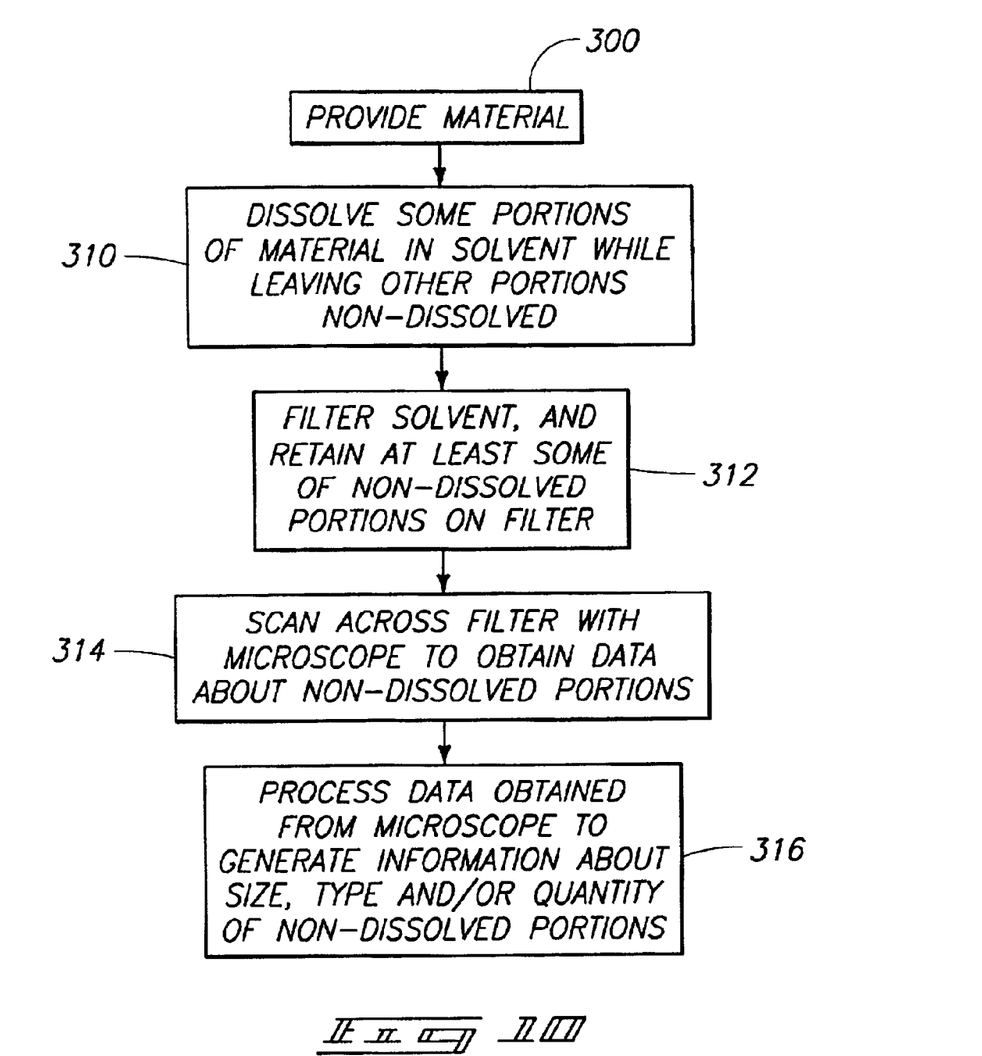
FIG. 10 is a flow chart diagram of a particular processing sequence of the present invention.

FIG. 10 is a flow chart description of a particular embodiment of the present invention. In the initial step 300 of FIG. 10, a material is provided. In step 310, some of the material is dissolved in a reagent, while other portions of the material are left non-dissolved. In step 312, the solution is filtered, and at least some of the non-dissolved portion of the material is retained on the filter. In step 314, a microscope is utilized to scan across a surface of the filter to obtain data about the non-dissolved portions. Finally, in step 316, the data obtained with a microscope is processed to generate information about one or more of the size, type and quantity of the non-dissolved portions. The processing described with reference to the flow chart of FIG. 10 can be accomplished utilizing methodology described with reference to FIGS. 2–9.

Although the invention is described above for analyzing solid materials provided in block form, it is to be understood that the invention comprises embodiments in addition to those specifically described above. For instance, the invention can be utilized for analyzing fluids. Specifically, fluids (either gas or liquid) can be passed through a filter. The filter can retain particulates that had been present in the fluids, and the particulates can be studied utilizing the procedures described herein. Also, the invention can be utilized for analyzing powdered materials. If powdered materials are to be analyzed, it can be preferable to dispense with the pre-etching procedure described with reference to FIG. 1. Further, although the invention is described as process for studying the bulk properties of a block of material (i.e., the surface of the block is removed with a pre-etch prior to analysis), the invention can also be utilized to study surface properties. If surface properties are to be studied, the pre-etch solution can be passed through a filter and microscopically analyzed with the pre-etch procedures described above. Further, depth profiling of a sample can be accomplished by incrementally etching a sample and analyzing the solutions formed during the incremental etching.

It is to be understood that numerous materials can be analyzed by methodology of the present invention, including, for example, materials comprising an organic matrix. In particular applications of the present invention, an organic matrix material can be dissolved in a reagent which is reactive for the material (such as, for example, an acid), or a reagent which is a solvent for the material (such as, for example, an organic solvent). In preparing and analyzing samples utilizing methods of the present invention, it is preferable to alleviate contamination of the samples by environmental particles. Accordingly, solutions are preferably filtered before use, glassware is preferably cleaned the day of use and stored upside down, and solutions are preferably kept covered prior to, and during analyses. To further alleviate contamination, processes of the present invention can be conducted in a so-called "clean room" (i.e., a room in which air-borne particulates are filtered from the atmosphere).

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A method of generating information about impurities present in a metal composition utilizing a microscope, comprising:

utilizing a reagent to selectively dissolve a portion of the composition relative to at least some impurities present in the metal composition, the dissolved portion forming a solution with the reagent; the impurities being at least two different types; one of the at least two types being a first type comprising a first material, and another of the at least two types being a second type comprising a second material, the second material differing from the first material;

filtering the solution through a substrate, at some of the first and second types of the impurities being retained on the substrate during the filtering;

after the filtering, altering at least one of a chemical property and a physical property of at least some of the impurities retained on the substrate to modify a light absorbing property;

scanning across at least a portion of the substrate with a light microscope, the scanning comprising automated displacement of the substrate relative to an observing portion of the microscope along a grid pattern, the microscope obtaining data about the impurities at locations along the grid pattern, the data including a relative darkness of the impurities relative to a background defined by the substrate; the first type of impurities being darker then the background and the second type of impurities being lighter than the background; and processing the data obtained by the microscope to generate information about the size, quantity and type of the impurities.

2. The method of claim 1 further comprising displaying results of the processing as a histogram showing impurities by one or more of type, size and quantity.

3. The method of claim 1 wherein the processing of the data obtained by the microscope comprises digital image processing.

4. The method of claim 1 wherein the dissolved portion of the metal composition comprises a mixture of aluminum and copper, and wherein the reagent is an acid comprising a mixture of hydrochloric acid and nitric acid.

5. The method of claim 1 wherein the first type of impurities predominately comprise carbon and wherein the second type of impurities predominately comprise one or more oxides.

* * * * *

UNITED STATES PATENT AND TRADEMARK OFFICE
CERTIFICATE OF CORRECTION

PATENT NO.    : 6,803,235 B1
DATED         : October 12, 2004
INVENTOR(S)   : Mize et al.

It is certified that error appears in the above-identified patent and that said Letters Patent is hereby corrected as shown below:

Column 6,
Line 32, replace "vessel 10" with -- vessel 110 --.

Column 8,
Line 11, replace "tens" with -- lens --.

Signed and Sealed this

Thirty-first Day of May, 2005

JON W. DUDAS
*Director of the United States Patent and Trademark Office*